(12) United States Patent
Fago et al.

(10) Patent No.: US 8,439,863 B2
(45) Date of Patent: May 14, 2013

(54) METHODS FOR CONTROLLING MEDICAL FLUID INJECTIONS

(75) Inventors: Frank M. Fago, Mason, OH (US);
James E. Knipfer, O'Fallon, MO (US)

(73) Assignee: Mallinckrodt LLC, Hazelwood, MO (US)

( * ) Notice: Subject to any disclaimer, the term of this patent is extended or adjusted under 35 U.S.C. 154(b) by 726 days.

(21) Appl. No.: 12/445,501

(22) PCT Filed: Apr. 28, 2008

(86) PCT No.: PCT/US2008/061722
§ 371 (c)(1),
(2), (4) Date: Apr. 14, 2009

(87) PCT Pub. No.: WO2008/137375
PCT Pub. Date: Nov. 13, 2008

(65) Prior Publication Data
US 2011/0166441 A1     Jul. 7, 2011

Related U.S. Application Data

(60) Provisional application No. 60/916,039, filed on May 4, 2007.

(51) Int. Cl.
*A61M 31/00* (2006.01)

(52) U.S. Cl.
USPC .............. 604/67; 600/431; 604/151; 604/154

(58) Field of Classification Search .......... 600/407–433, 600/437–469, 473–480; 604/500–522, 64–67, 604/151–154; 340/10.1, 618, 572.1, 572.7, 340/572.8; 235/385
See application file for complete search history.

(56) References Cited

U.S. PATENT DOCUMENTS

| | | | |
|---|---|---|---|
| 5,553,619 A | 9/1996 | Prince | |
| 5,800,397 A | 9/1998 | Wilson | |
| 6,488,660 B1 | 12/2002 | Futterknecht | |
| 7,413,123 B2 * | 8/2008 | Ortenzi | 235/385 |
| 7,588,189 B2 * | 9/2009 | Fago et al. | 235/462.46 |
| 7,621,892 B2 * | 11/2009 | Fago et al. | 604/151 |
| 7,698,180 B2 * | 4/2010 | Fago et al. | 705/28 |
| 7,725,168 B2 * | 5/2010 | Neer et al. | 600/432 |
| 7,859,473 B2 * | 12/2010 | Gibson | 343/742 |
| 7,898,416 B2 * | 3/2011 | Fago et al. | 340/572.1 |
| 7,963,936 B2 * | 6/2011 | Ortenzi et al. | 604/65 |
| 7,975,922 B2 * | 7/2011 | Fago et al. | 235/451 |
| 8,035,517 B2 * | 10/2011 | Gibson | 340/572.1 |
| 8,180,434 B2 * | 5/2012 | Gibbs et al. | 600/432 |
| 8,251,071 B2 * | 8/2012 | Neer et al. | 128/898 |
| 8,277,416 B2 * | 10/2012 | Gibbs et al. | 604/151 |
| 8,282,595 B2 * | 10/2012 | Wagner | 604/67 |
| 8,317,099 B2 * | 11/2012 | Perkins et al. | 235/385 |

(Continued)

FOREIGN PATENT DOCUMENTS

| | | |
|---|---|---|
| EP | 1932556 A1 | 6/2008 |
| WO | 2006096654 A2 | 9/2006 |
| WO | 2007032341 A1 | 3/2007 |

*Primary Examiner* — Sanjay Cattungal

(57) ABSTRACT

The present invention is directed to control of medical fluid injection systems. For instance, in some embodiments, an injection protocol may be initiated, and an actual flow rate of the medical fluid utilized in the injection protocol may be adjusted based, at least in part, on an inherent system elasticity of the injection system.

35 Claims, 3 Drawing Sheets

U.S. PATENT DOCUMENTS

| | | |
|---|---|---|
| 2003/0216643 A1 | 11/2003 | Zatezalo et al. |
| 2006/0079768 A1 | 4/2006 | Small et al. |
| 2006/0264898 A1 | 11/2006 | Beasley et al. |
| 2007/0191690 A1* | 8/2007 | Hasse et al. .................. 600/300 |
| 2007/0197974 A1* | 8/2007 | Gibson ......................... 604/189 |
| 2007/0208308 A1* | 9/2007 | Gibson et al. ................ 604/131 |
| 2007/0208445 A1* | 9/2007 | Gibson et al. ................ 700/115 |
| 2007/0225672 A1* | 9/2007 | Wagner ........................ 604/404 |
| 2007/0229266 A1* | 10/2007 | Gibson ..................... 340/572.1 |
| 2007/0235534 A1* | 10/2007 | Fago et al. .................... 235/385 |
| 2007/0238989 A1* | 10/2007 | Hasse et al. .................. 600/431 |
| 2007/0239112 A1* | 10/2007 | Fago et al. .................... 604/113 |
| 2007/0241883 A1* | 10/2007 | Fago et al. ................. 340/539.1 |
| 2007/0250414 A1* | 10/2007 | Fago et al. ...................... 705/28 |
| 2007/0257111 A1* | 11/2007 | Ortenzi ......................... 235/385 |
| 2007/0299421 A1* | 12/2007 | Gibson ......................... 604/506 |
| 2008/0033368 A1* | 2/2008 | Fago ............................. 604/189 |
| 2008/0147015 A1* | 6/2008 | Ortenzi et al. ................ 604/232 |
| 2008/0208042 A1* | 8/2008 | Ortenzi et al. ................ 600/432 |
| 2011/0060219 A1* | 3/2011 | Small et al. ................... 600/432 |

* cited by examiner

METHODS FOR CONTROLLING MEDICAL FLUID INJECTIONS

This application is a U.S. National Stage of PCT/US2008/061722, filed 28 Apr. 2008, which claims priority to U.S. provisional application Ser. No. 60/916,039 filed on 4 May 2007 entitled METHODS FOR CONTROLLING MEDICAL FLUID INJECTIONS.

FIELD OF THE INVENTION

The present invention generally relates to injections of medical fluids, and more particularly, to methods for controlling injections of such medical fluids.

BACKGROUND

It is well recognized that the appropriate dose for many medications is related to a number of variables, including, for example, the size, weight, and/or physiologic state of the patient being treated. This variation is readily apparent from the different recommended doses many medications have for adults and children. The appropriate dose of contrast media for a given medical imaging procedure also tends to be dependent upon the size and weight of the patient being examined as well as additional factors.

Although differences in dosing requirements for medical imaging procedures have been recognized, many conventional medical imaging procedures, including angiographic, computed tomography, magnetic resonance and ultrasound imaging, continue to use pre-set doses or standard delivery protocols for injecting contrast media for medical imaging procedures. Although using fixed protocols for delivery simplifies the procedure, providing the same amount of contrast media to patients of varying size and weight can produce very different results in image contrast and quality.

It is typically desirable to coordinate the time of the image acquisition with the time of greatest levels of contrast in the region of interest, in some instances, with respect to a threshold value. Many physiological factors can affect the start time and duration of a sufficient level of contrast in the region of interest. For example, because the cardiovascular system generally provides the means for circulation of contrast agent throughout the body after it is injected, a patient's cardiac output can have a significant effect on the distribution of the contrast agent as well as the time taken for the contrast agent to reach a particular organ or vessel.

Current understanding of intravenous contrast enhancement is further complicated by multiple interacting factors. As such, in many respects, contrast enhancement still relies heavily on the experience and intuition of the physician rather than rigorous, quantitative analysis of the mechanism of contrast enhancement.

SUMMARY

In certain embodiments, the present invention relates to systems and methods for promoting injection of medical fluid at actual flow rates that substantially correspond with desired flow rates. In certain embodiments, the present invention relates to systems and methods for promoting injection of contrast media at flow rates sufficient to enable achievement of desired levels of patient enhancement during imaging. In the above-mentioned embodiments, elasticity of the injection system (e.g., various components thereof) is taken into account when controlling (e.g., adjusting) the actual flow rate of the injection system so that the desired flow rate and/or patient enhancement can be achieved.

Certain exemplary aspects of the invention are set forth below. It should be understood that these aspects are presented merely to provide the reader with a brief summary of certain forms the invention might take and that these aspects are not intended to limit the scope of the invention. Indeed, the invention may encompass a variety of aspects that may not be explicitly set forth below.

One aspect of the present invention is directed to a method of operation for a medical fluid injection system. In this method, an injection protocol that includes a desired flow rate for the medical fluid (e.g., contrast media) is initiated. An actual flow rate of the medical fluid is adjusted to follow the desired flow rate for the medical fluid based, at least in part, on an inherent system elasticity of the injection system.

Another aspect of the invention is directed to a method of operation for a medical imaging system that includes a medical fluid injection assembly and a medical imaging device. In this method, an injection protocol corresponding to a desired level of patient enhancement is initiated. Based, at least in part, on an inherent elasticity of the injection assembly, an actual flow rate of the injection protocol is adjusted to achieve the desired level of patient enhancement.

Various features discussed below in relation to one or more of the exemplary embodiments may be incorporated into any of the above-described aspects of the present invention alone or in any combination. Again, the brief summary presented above is intended only to familiarize the reader with certain aspects and contexts of the present invention without limitation to the claimed subject matter.

BRIEF DESCRIPTION OF THE FIGURES

Various features, aspects, and advantages of the present invention will become better understood when the following detailed description is read with reference to the accompanying figures in which like characters represent like parts throughout the figures, wherein.

DETAILED DESCRIPTION OF EXEMPLARY EMBODIMENTS

One or more specific embodiments of the present invention will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of the present invention (E.G., the exemplary embodiments(s) thereof), the articles "a", "an", "the" and "said" are intended to mean that there are one or more of the elements. The terms "comprising", "including" and "having" are intended to be inclusive and mean that there may be additional elements other than the listed elements.

Many injection systems used in medical scanning procedures have an inherent elasticity due to compression of an associated syringe plunger, expansion of an associated syringe barrel, and/or expansion of associated extension tubing. This elasticity causes the output of the injection to "smooth out" and lag behind the input. As such, input speeds of the syringe plunger may need to be exaggerated in order to produce the desired output. For example, a pressure increase is required to increase the flow rate; however, some of the energy resulting from the pressure increase is stored in the elasticity of the system. To compensate for this elasticity, the injector will need to increase speed faster than it would if the system were not elastic in order to accurately output the desired flow rate. Conversely, in order to reduce the injection rate, the injector must slow down sooner in order to allow for stored energy to diminish. In extreme cases, the motor may actually need to reverse direction.

Flow rate correction factors for the injector may be determined during a test injection. The injector may sense the type of syringe being used so a predetermined elasticity factor may be saved for each syringe type. During the test injection, the injector may determine parameters influencing the output rate of the injector by analyzing a pressure profile produced during the test injection. Correction factors to the injector motor speed may also be determined based on the analysis of the pressure profile. The injector may analyze the corrected speed(s) of the motor to ensure that it does not exceed the design limits of the injector.

Figure 1:
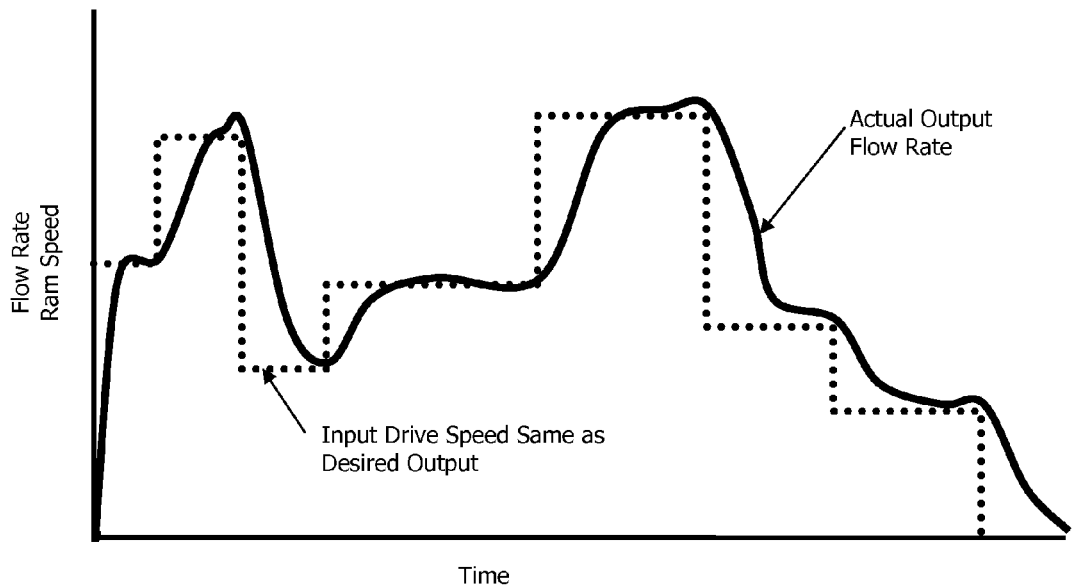
FIG. 1 shows an exemplary injection profile and a lagging output flow rate.
Figure 2:
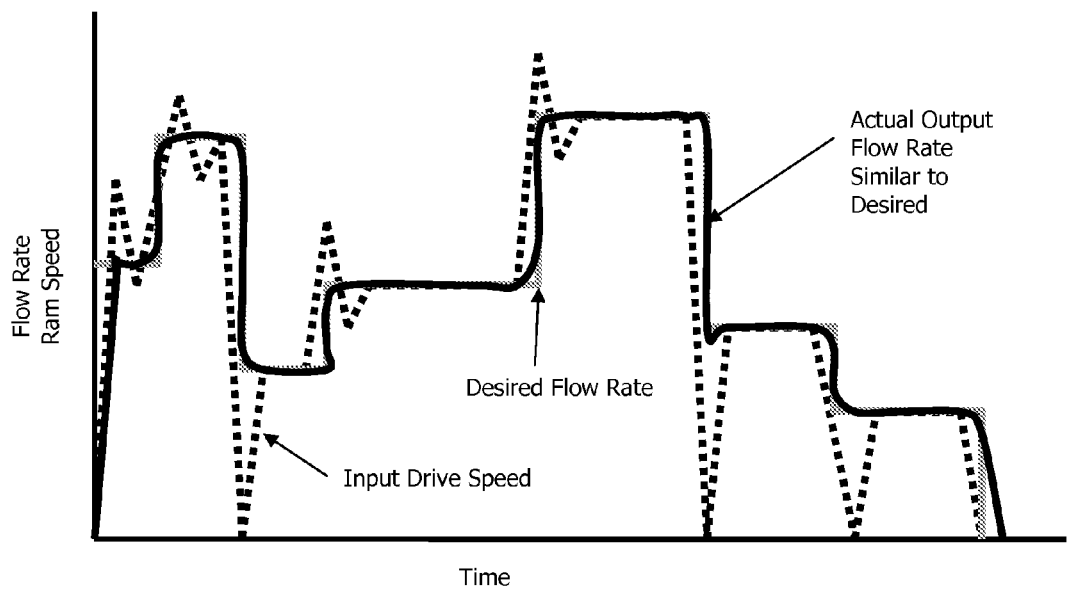
FIG. 2 shows the exemplary injection profile and an adjusted injector drive speed to correct the output flow rate.

An exemplary injection protocol may be seen in FIG. 1. This figure illustrates how the actual output flow rate from the injector lags behind the desired output of the injection protocol. Using the results of the analysis of the pressure profile created during the test injection, correction factors to the input speed of the drive ram in the injector may be determined which will allow the output flow rate to more closely match the desired flow rate of the injection protocol. An example of the correction factors adjusting the drive ram speed may be seen in FIG. 2. The correction factors exaggerate the input drive speed in order to compensate for the energy stored in the inherent elasticity of the injector system and allow the output to more closely follow the desired flow rate of the injector protocol.

Figure 3:
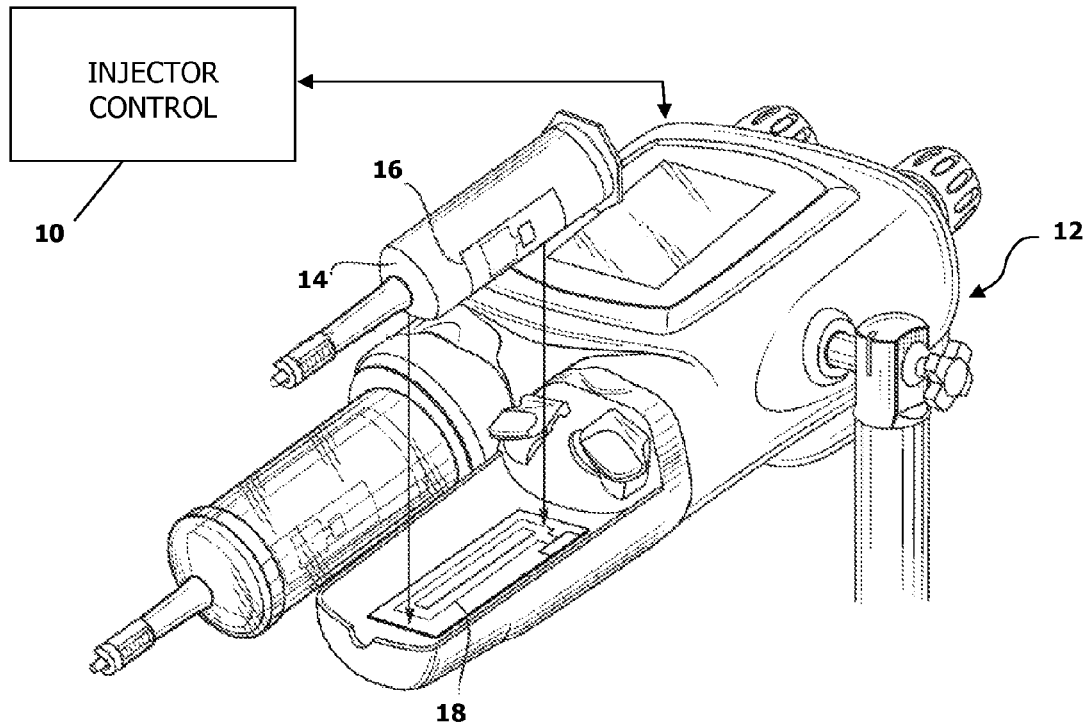
FIG. 3 shows an exemplary injector having a syringe and injector control.

The inherent elasticity of the injector system is related to the syringe and tubing being used. In addition, the viscosity of the contrast media and the diameter of the catheter (not shown) affect the output flow rate of the injector. Referring now to FIG. 3, the injector receives a syringe 14, which in turn is connected to a catheter to deliver contrast media to a patient. In some embodiments, the syringe that is inserted into the injector 12 may contain an RF-ID data tag 16, communicating with an antenna 18 connected and communicating with the injector 12, which may contain information related to that particular syringe. For example, the RF-ID data tag 16 may contain the type of syringe and contrast media therein. This identification information may allow an injector control 10 to easily retrieve elasticity data gathered from the analysis of the pressure profile, created during the test injection. The RF-ID data tag 16 may also contain data related to the pressure profile and syringe elasticity. In other embodiments, a physician or technician may manually enter the syringe and tubing information directly into the injector control 10. A library of elasticity data for each of the syringes and tubing that are used with the injector may be stored in the injector control 10 for later use.

Figure 4:
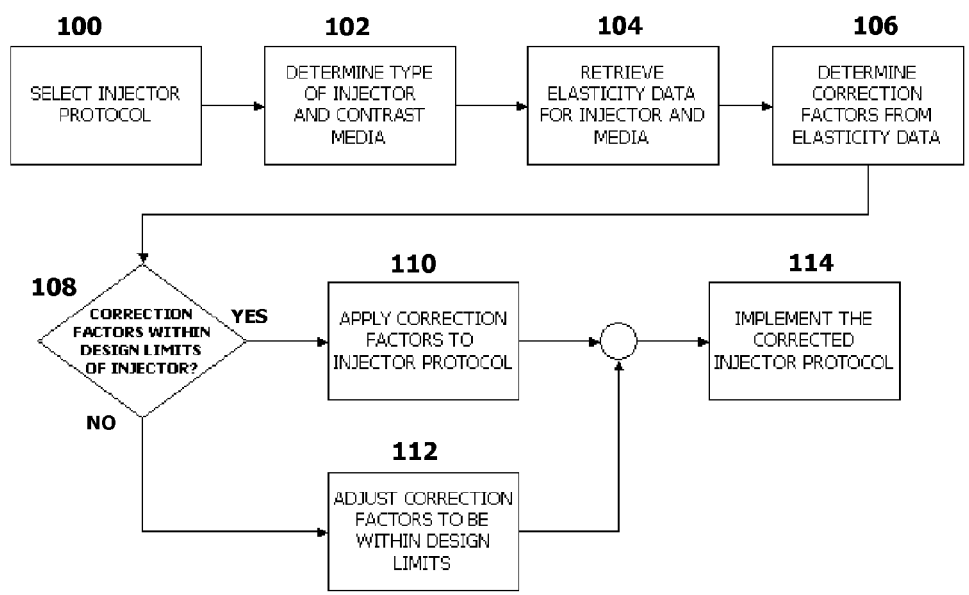
FIG. 4 is a flow chart of a method to deliver a specific injection profile.

Referring now to FIG. 4, an injector protocol may be selected in block 100 that is consistent with the medical procedure performed on a patient with an imaging system. A syringe containing contrast media is inserted into the injector. At this point, in block 102, a determination of the type of syringe, the type of contrast media, and other injector parameters is made in order to locate elasticity data for the injector. This data may be stored, in some embodiments, in the injector control. Once the type of injector with syringe and contrast has been determined, elasticity data is retrieved in block 104. A series of correction factors is determined in block 106 from predictions made based on the desired output waveform shape and the elasticity data for the injector. The correction factors will be applied to the input drive ram speed in order to adjust the actual output flow rate, to closely follow the desired flow rate. The correction factors exaggerate the input drive ram speed, which may overshoot the actual desired output rates. Exaggerating the drive speed of the injector may compensate for the inherent lag in the fluid. In some situations, this may require that the drive ram speed be faster than the increase in the desired flow rate of the system. In other cases, the speed of the drive ram may be slower than the desired flow rate. In some extreme cases, it may be necessary to reverse the direction of the drive ram in order to obtain the proper output flow rate profile.

Before the correction factors may be applied to the input drive, a check should be done in block 108 to determine if, once the correction factors are applied, the input drive ram speed is within the design limits of the injector. If the drive speed with the correction factors applied is outside of the design limits of the injector (no branch of decision block 108), then the correction factors are adjusted in block 112 to be within the design limitations. After these factors have been adjusted, the factors are then applied to the injector protocol in block 110. Once the input drive speed has been adjusted so that the desired flow rate may be met, the injector protocol is ready to be implemented in an injection to the patient.

System elasticity may be based on many factors related to different components of the injection system. For example, the compression of the syringe plunger may contribute to the elasticity as it encounters the incompressible fluid of the contrast media. Similarly, the barrel of the syringe may contribute to the elasticity of the overall system as the barrel may expand slightly due to the sudden increase in pressure applied by the plunger. In addition to the syringe and the plunger, which are part of the injector, extension tubing and catheter tubing connecting the injection system to the patient may also have an inherent elasticity, allowing the tubing to expand due to the increase in the pressure applied to the contrast media, contributing to the elasticity of the system.

The elasticity of the injector system may be determined from analyzing a pressure profile resulting from a test injection. The test injection injects a small amount of contrast media into a patient while measuring the pressure profile. Analysis of this pressure profile enables an algorithm in or communicating with the injector control to predict the lags in the delivery of the contrast media due to the elasticity in the system. From these predictions, the speed of the drive ram contacting the plunger may be adjusted to compensate for the inherent lags. After the pressure profile has been analyzed, the results of that profile and the components contributing to the elasticity of the system may be stored in the injector control, for example, for later use with other patients. Once a library of syringes, injectors, tubing and other components has been built, the need for further test injections may not be necessary.

In one aspect of the present invention, as discussed above, an injection protocol may be selected by a technician or by a physician with experience in the imaging systems in order to obtain a clear image of the portion of the body of the patient of interest. In another aspect of the present invention, the imaging system may also be able to send injection protocol information to the injector in order to make real-time adjustments to the injection rate of the contrast media during an imaging procedure.

Figure 5:
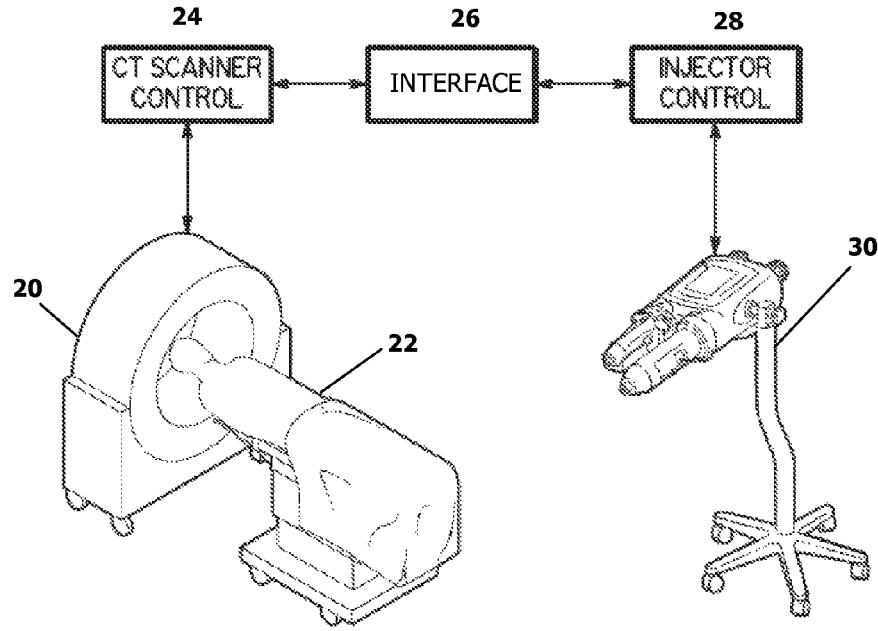
FIG. 5 shows an exemplary CT scanner with a control in communication with an exemplary injector.

Referring now to FIG. 5, an imaging system, such as a CT scanner 20, to be used in a medical procedure on patient 22 may communicate using a common interface 26 with the injector 30. A control for the CT scanner 24 communicates through the interface 26 to a control for the injector 28 in order to increase or decrease the injection rate of the contrast media to achieve clear images. In some embodiments, this communication may be accomplished through a CAN interface. In other embodiments, other interfaces such as RS-232 or RS-422 may be used. As will be apparent to those skilled in the art, in addition to these three communication protocols, any protocol that would allow the injector and the imaging system to communicate would be sufficient.

Figure 6:
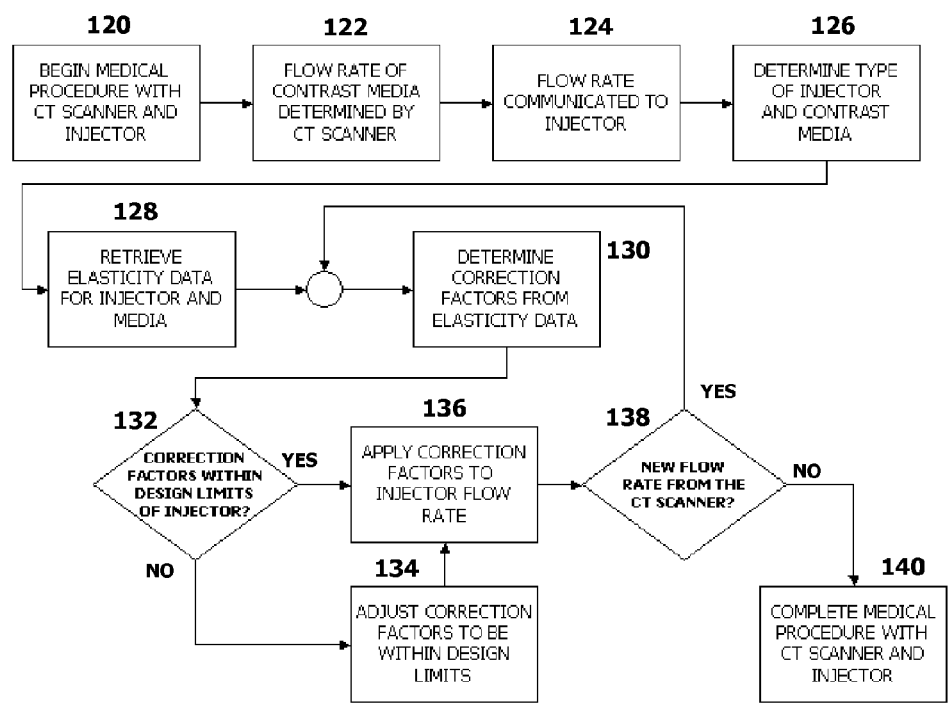
FIG. 6 is a flow chart of another method to deliver a specific injection profile.

Referring now to FIG. 6, the medical procedure utilizing a CT scanner and an injector begins in block 120. The imaging system used in this particular embodiment is a CT scanner, although other imaging systems may also be used. In other embodiments, the imaging system may comprise a magnetic resonance imaging system, an angiographic imaging system, or an ultrasound imaging system. During the imaging process in block 122 the CT scanner may determine an optimum flow rate of the contrast media. This flow rate is communicated to the injector control through a common interface in block 124. After the flow rate information has been communicated to the injector control, the type of syringe, contrast media and tubing may be determined in block 126. Once the components have been identified in block 128, the elasticity data for the injector system may be retrieved. Similar to above, a set of correction factors is then determined from the component elasticity data and from flow rate data sent from the imaging system in block 130.

Again, the correction factors are analyzed to determine if they are within the design limitations of the injector. If the correction factors would cause the injector to operate outside of the design limitations, in block 134, these correction factors would be adjusted to be within design limitations. The correction factors are then applied to the injector drive ram speed in block 136 and the output flow rate of the injector is modified accordingly. If new or additional flow rates are available from the CT scanner (yes branch of decision block 138), then a new set of correction factors may be determined based on the new flow rate and the process continues. If no new flow rate information is available from the scanner (no branch of decision block 138), then the medical procedure completes with the CT scanner and the injector.

As various changes could be made in the above-described aspects and exemplary embodiments without departing from the scope of the invention, it is intended that all matter contained in the above description shall be interpreted as illustrative and not in a limiting sense.

What is claimed is:

1. A method of operation for a contrast media injection system, the method comprising:
    initiating an injection protocol comprising a desired flow rate for the contrast media; and
    adjusting an actual flow rate of the contrast media during execution of the injection protocol, wherein the adjusting comprises using a series of correction factors to follow the desired flow rate for the contrast media, wherein the series of correction factors are based on: a) a desired output waveform shape associated with the desired flow rate; and b) inherent system elasticity data.

2. The method of claim 1, wherein the adjusting comprises accounting for elasticity of a syringe plunger.

3. The method of claim 1, wherein the adjusting comprises accounting for elasticity of a syringe barrel.

4. The method of claim 1, wherein the adjusting comprises accounting for elasticity of a contrast media container.

5. The method of claim 1, wherein the adjusting comprises accounting for elasticity of extension tubing.

6. The method of claim 1, wherein the inherent system elasticity data is based, at least in part, on elasticity data related to a container, syringe, tubing, or a combination thereof utilized in the system.

7. The method of claim 1, wherein the inherent system elasticity data is based, at least in part, on viscosity data related to the contrast media.

8. The method of claim 1, wherein the series of correction factors is dependent upon viscosity of the contrast media.

9. The method of claim 1, wherein the series of correction factors is dependent upon catheter size.

10. The method of claim 1, wherein the adjusting comprises increasing an actual motor speed of the injection system more than a motor speed corresponding with the desired flow rate.

11. The method of claim 1, wherein the adjusting comprises decreasing an actual motor speed of the injection system more than a motor speed corresponding with the desired flow rate.

12. The method of claim 1, wherein the adjusting comprises reversing a direction of motion of a motor of the injection system.

13. The method of claim 1, further comprising reading elasticity data from a data tag of a component used by the injection system, wherein the inherent system elasticity data comprises the read elasticity data.

14. The method of claim 1, further comprising retrieving the inherent system elasticity data from a library stored by the injection system.

15. The method of claim 1, further comprising:
    identifying a component used by the injection system; and
    retrieving elasticity data on the component using the identifying, wherein the inherent system elasticity data comprises the retrieved elasticity data.

16. The method of claim 1, further comprising predicting lags in a delivery of contrast media due to elasticity of the injection system, wherein the adjusting uses the predicting.

17. The method of claim 16, wherein the predicting comprises using an algorithm.

18. The method of claim 1, further comprising;
    performing a test injection prior to the initiating; and
    determining the inherent system elasticity data from the test injection.

19. The method of claim 18, wherein the determining comprises analyzing a pressure profile resulting from the test injection.

20. The method of claim 18, wherein the performing and the determining each occur prior to the initiating.

21. The method of claim 1, further comprising:
   sensing an elastic component associated with the injection system; and
   retrieving a predetermined elasticity factor for the component.

22. The method of claim 21, where the component comprises a contrast media container, a syringe, tubing, or a combination thereof.

23. The method of claim 21, wherein the sensing comprises reading data from an RF-ID data tag that contains information about the component.

24. The method of claim 23, wherein the information comprises at least one of pressure profile data and elasticity data.

25. The method of claim 1, wherein the desired flow rate comprises a plurality of flow rates.

26. The method of claim 25, wherein the plurality of flow rates is communicated between the injection system and a medical imaging system via a common interface.

27. The method of claim 26, wherein the common interface is a CAN interface.

28. The method of claim 26, wherein the common interface is an RS-232 interface.

29. The method of claim 26, wherein the common interface is an RS-422 interface.

30. The method of claim 1, wherein at least a portion of the injection protocol is carried out during medical imaging of the patient.

31. The method of claim 30, wherein the medical imaging comprises CT scanning of the patient.

32. The method of claim 30, wherein the medical imaging comprises magnetic resonance imaging of the patient.

33. The method of claim 30, wherein the medical imaging comprises angiographic imaging of the patient.

34. The method of claim 30, wherein the medical imaging comprises ultrasound imaging of the patient.

35. The method of claim 30, wherein the medical imaging comprises optical imaging of the patient.

* * * * *